United States Patent
Rousseau et al.

[11] Patent Number: 5,972,003
[45] Date of Patent: Oct. 26, 1999

[54] SINGLE-FREE LIGATION CLIP MODULE

[75] Inventors: Robert A. Rousseau, New Milford; Ernest N. Corrao, Jr., Bethel, both of Conn.

[73] Assignee: Sherwood Services AG, Schaffhausen, Switzerland

[21] Appl. No.: 08/942,073

[22] Filed: Oct. 1, 1997

[51] Int. Cl.⁶ .................................................. A61B 17/10
[52] U.S. Cl. ........................ 606/142; 606/139; 606/151
[58] Field of Search ..................... 606/139, 142, 606/143, 144, 151; 227/901

[56] References Cited

U.S. PATENT DOCUMENTS

| | | | |
|---|---|---|---|
| 4,325,377 | 4/1982 | Boebel | 128/326 |
| 4,759,364 | 7/1988 | Boebel | 128/326 |
| 5,015,249 | 5/1991 | Nakao et al. | 606/142 |
| 5,163,945 | 11/1992 | Ortiz et al. | 606/142 |
| 5,354,304 | 10/1994 | Allen et al. | 606/142 |
| 5,366,459 | 11/1994 | Yoon . | |
| 5,447,513 | 9/1995 | Davison et al. | 606/143 |
| 5,474,566 | 12/1995 | Alesi et al. | 606/139 |
| 5,478,353 | 12/1995 | Yoon . | |
| 5,520,701 | 5/1996 | Lerch . | |
| 5,634,932 | 6/1997 | Schmidt | 606/157 |

*Primary Examiner*—Michael Buiz
*Assistant Examiner*—Tina T. D. Pham

[57] ABSTRACT

A ligation clip module of unitary construction adapted for use with a ligation clip applicator for housing and applying a ligation clip around a vessel. The ligation clip module comprises a module housing, ligation clip and pusher. The module housing forms a cavity having a first and second channels therein that house the ligation clip and pusher therein. The ligation clip includes a Y-shaped clip track having two extended arms and a U-shaped clip body with an extended slot for slidably engaging the clip track and closing the arms of the clip track about the vessel during application by the applicator. The module housing includes a frusto-conical section with opposing tapered beveled portions that enhance visibility along the longitudinal axis of the module housing and a reduced diameter section that is adapted for attachment to the applicator. In operation, the module is attached to a distal neck portion of the applicator wherein an advancing element of the applicator forces the pusher inside the module housing forward through the two channels. The pusher then engages the proximal end of the clip body which slides over the clip track, thereby ligating the vessel between the two arms of the track.

22 Claims, 10 Drawing Sheets

SINGLE-FREE LIGATION CLIP MODULE

BACKGROUND OF THE INVENTION

1. Field of the Invention

The present invention relates generally to a medical instrument for use with a surgical ligation clip applicator. More particularly, the invention is directed to a unitary single-fire module for housing a two-part ligation clip for securing and closing the two-part ligation clip around a vessel to be occluded.

2. Prior Art

A surgical ligation clip is used to compress a severed blood vessel to stop the flow of blood. The single-fire module of the subject invention is particularly designed for housing and applying a two-part surgical ligation clip. The first part comprises generally a Y-shaped clamp or track having two extended arms for fitting around a vessel to be ligated. The second part is a U-shaped clip body with an extended slot for slidably engaging the track and closing the arms of the clip track about the vessel. Ligation clips of this type are disclosed in U.S. Pat. No. 4,590,937 and in U.S. Pat. No. 5,306,283, both of which are assigned to the assignee of the subject invention and are incorporated herein by reference.

There are many types of known modules for use with mechanical applicators for closing a conventional ligation clip around a vessel. The module can be attached to the distal end of the mechanical applicator by a spring loaded latch as disclosed in U.S. Pat. No. 5,354,304 or other type of latching means which attachably secures the module to the applicator. Several examples of other known applicators include the so-called push-pull type, which uses a plunger or a piston, or a fulcrum type applicator having scissors-like or pliers-like handle. U.S. Pat. No. 5,354,304 discloses a preferred single-fire mechanical applicator for use with the subject invention and is incorporated herein by reference.

U.S. Pat. No. 5,354,304 further discloses a prior art single-fire module for housing the two-part ligation clip prior to application. The prior art module holds the clip track of the ligation clip in a stationary position as an advancing pusher at the proximal end of the module moves the sliding clip body of the ligation clip forward in order to compress the clip track around a vessel of a patient. The prior art module comprises two substantially identical cartridge halves that are joined together by integral alignment pins that align the two halves together so that the two halves may be welded securely together during manufacturing. Upper and lower metal latches, each having an integral spring and opposing trunions, are housed inside the middle portion of the module and pivot in holes formed in each cartridge halve. The integral springs press against ribs also formed inside each cartridge halve and urge the proximal ends of the metal latches toward each other so that the metal latches are compressively housed inside the module. A prior art pusher is also provided at a proximal end opening of the module for actuating the two-part ligation clip when the applicator is actuated by the user. The latches are also provided with a V-shaped end portion which engages opposing grooves formed on either side of the prior art pusher for retaining the pusher inside the cartridge housing.

Although the above prior art module provides an efficient and advantageous means of occluding a vessel with a two-part ligation clip, several disadvantages remain. The prior art module is costly to manufacture because of the different parts that must be manufactured and put together during assembly. Specifically, the metal latches with their cantilevered compression springs are costly to manufacture and time-consuming to assemble into the prior module since this must be done manually. Further, the prior art module can tend to jam due to the metal latches being improperly assembled or defects that occur during manufacturing of the metal latches. Finally, the prior art module has a wide profile along its longitudinal axis which may block or interfere with the user's view of the vessel during application of the two-part clip, with the applicator.

There therefore exists a need in the art for a unitary single-piece module for housing and applying a ligation clip in which the module is of a single unitary design with no separate parts therein. There also exists a need in the art for a single-piece module that is less costly to manufacture and requires little or no assembly during manufacturing. Finally, there also exists a need for a single-piece module housing having a low profile that permits clearer viewing of a vessel during ligation.

SUMMARY OF THE INVENTION

Accordingly, it is a general object of the present invention to provide an improved ligation clip module for housing a ligation clip.

It is another object of the present invention to provide a module for housing a two-part ligation clip, and more particularly, two-part ligation clips of the type disclosed in U.S. Pat. Nos. 4,590,937 and 5,306,283.

It is still another object of the present invention to provide a module for attachment to a ligation clip applicator, and more particularly, a ligation clip applicator of the type disclosed in U.S. Pat. No. 5,354,304.

It is still another object of the present invention to provide a module housing of unitary design and manufacture that requires no manual assembly during manufacturing and utilizes less parts to manufacture.

It is still another further object of the present invention to provide a module that is less costly to manufacture.

It is still another object of the present invention to provide a module that does not jam during application of the ligation clip to a vessel during ligation.

It is yet another object of the present invention to provide a module that forms a low profile for better viewing along its longitudinal axis.

In accordance with one aspect of the invention, a module for mounting a two-part ligation clip comprises a unitary module housing, a holding means formed as part of the cartridge housing for holding a first part of the ligation clip in a stationary position, and a sliding means, also housed in the cartridge housing, for advancing a second part of the ligation clip about the first part during application.

The subject invention thus provides a module for mounting the ligation clip onto an applicator. The module is preferably made primarily of a hard resilient plastic or other similar low cost material and is disposable. In addition, different size modules for mounting various size ligation clips can be interchangeably connected to the same, reusable applicator. The module is connected to a slender, elongated hollow shaft that houses a slidable advancer. A handle assembly connected to the other end of the shaft actuates the advancer to slide it axially within the shaft and engage a pusher disposed in the module. The module holds the clip track of the ligation clip in a stationary position as the advancing pusher moves the sliding clip body forwardly to compress the clip track around a vessel.

These and other objects, aspects, features and advantages of the present invention will become apparent from the following detailed description of the preferred embodiments taken in conjunction with the accompanying drawings.

DETAILED DESCRIPTION OF THE PREFERRED EMBODIMENTS

As noted above, the single-fire ligation clip module 23 of the present invention is specifically designed to house and apply a two-part ligation clip of the types described in U.S. Pat. Nos. 4,590,937 and 5,306,283, both of which are incorporated herein by reference. For convenience, however, the invention will be described with reference to the two-part ligation clip described in U.S. Pat. No. 5,306, 283. Further, the module 23 of the present invention can be used with the ligation clip applicator described in U.S. Pat. No. 5,354,304, which is also incorporated herein by reference.

Figure 1:
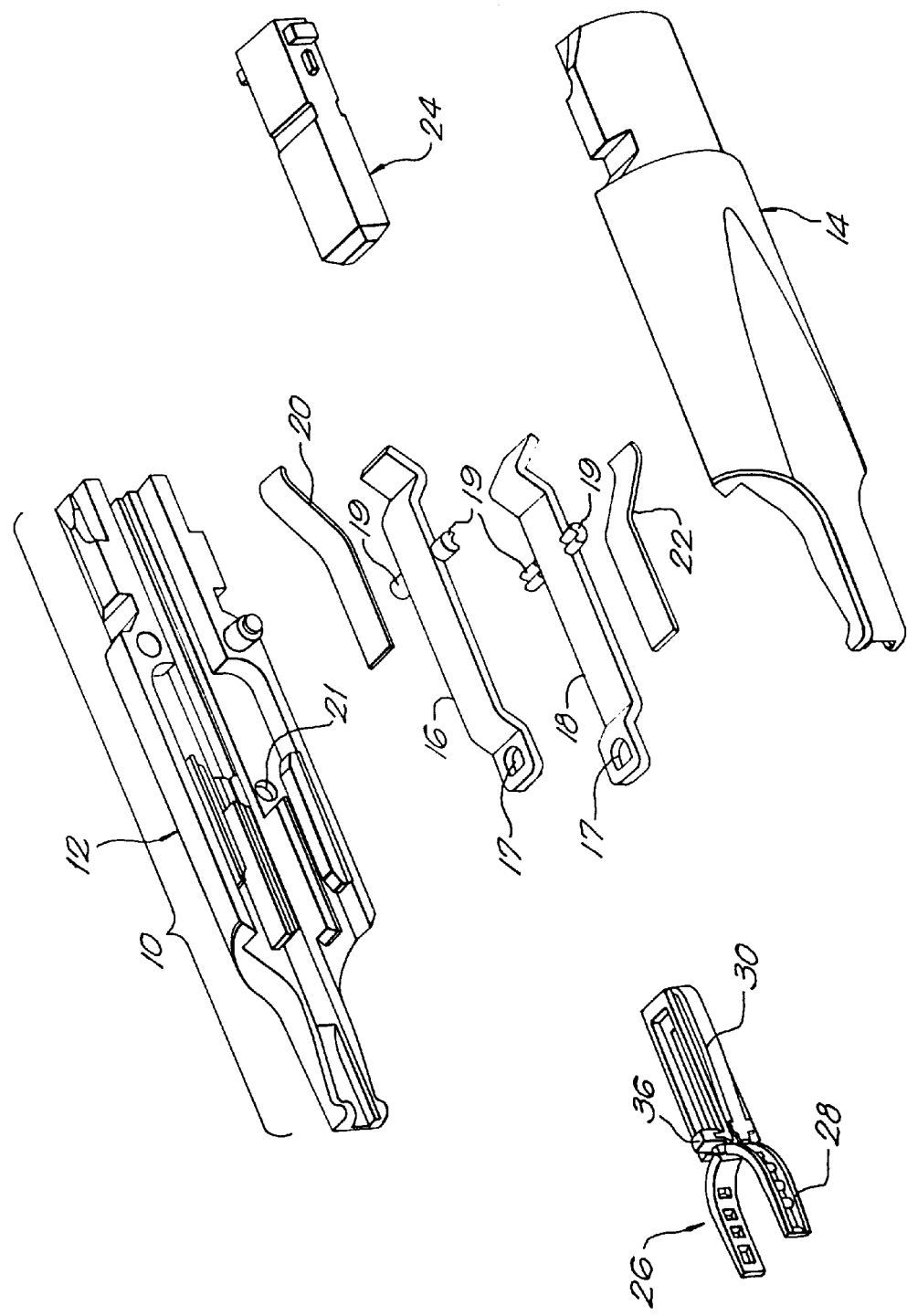
FIG. 1 is an exploded perspective view of a prior art ligation clip module.

A prior art single-fire ligation clip module is shown in FIG. 1 and comprises a cartridge housing 10 that includes substantially identical first and second cartridge halves 12 and 14 that are joined together by engaging the integral alignment pins (not shown) in one cartridge half and welding or otherwise securing the halves 12 and 14 together. First and second latches 16 and 18 each have an first and second integral springs 20 and 22, respectively, and opposing trunions 19 which pivot in holes 21 in both cartridge halves 12 and 14. First and second integral springs 20 and 22 press against the interior surface of each cartridge half and urge the proximal ends of the latches 16 and 18 toward each other. First and second latches 16 and 18 further include latch holes 17 at its distal end which are connected to a post 36 of the ligation clip 26.

Ligation clip 26 comprises a U-shaped clip body 30 slidably connected to a Y-shaped clip track 28 through a post 36 located at the apex of the clip track 28. The post 36 extends and attaches to holes 17 of the first and second latches 16 and 18. The attachment of holes 17 to the post 36 keeps the clip track 28 stationary when the clip track 28 is being drawn into the clip body 30 during application.

A prior art pusher 24 rides a track provided in the opposing cartridge halves 12 and 14. The pusher 24 abuts against the proximal end of the clip body 30 in the initial assembled condition inside the cartridge housing 10 and is used to force the clip body 30 over the clip track 28 when actuated by the ligation clip applicator 92 (FIG. 7) during ligation.

Figure 2:
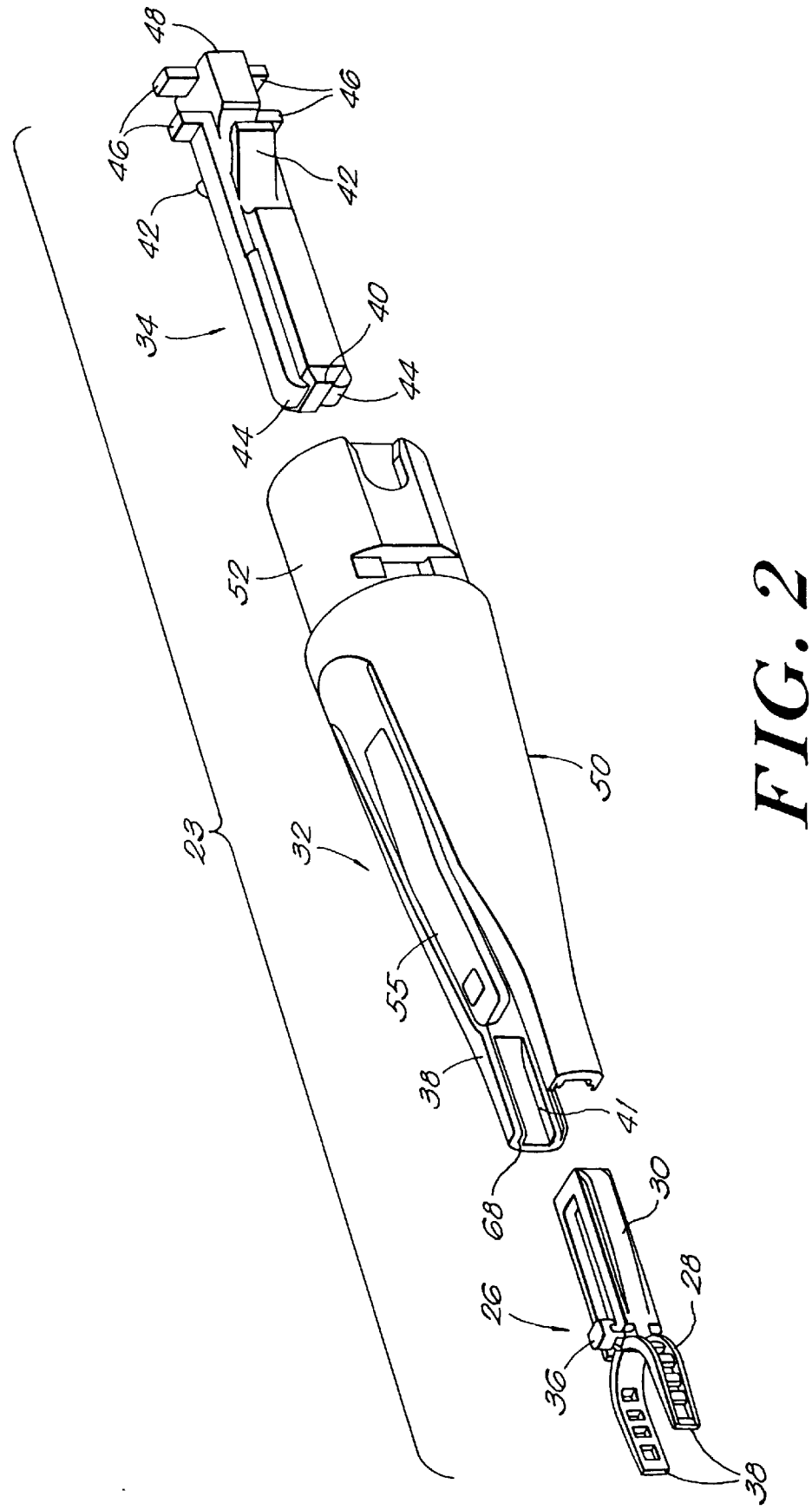
FIG. 2 is an exploded perspective view of the ligation clip module according to the present invention.

A module 23 according to the present invention is shown in FIG. 2. Module 23 comprises a unitary module housing 32 that comprises a frustoconical section 50 and a reduced diameter section 52. During manufacturing, a pusher 34 is placed into a cavity 65 at the proximal end of the module housing 32. Pusher 34 comprises a beveled front end 40 at its distal end and a rear portion 48 at its proximal end. Opposing radius surfaces 44 are formed on the top and bottom portions of pusher 34 while opposing wings 42 extend laterally at an acute angle from the side portions of the pusher 34. Further, two pairs of flanges 46 located at the proximal end of pusher 34 extend from the top and bottom of the pusher 34. Finally, a ligation clip 26 as described above is attached to the distal end of the pusher 26 during manufacturing.

Figure 3:
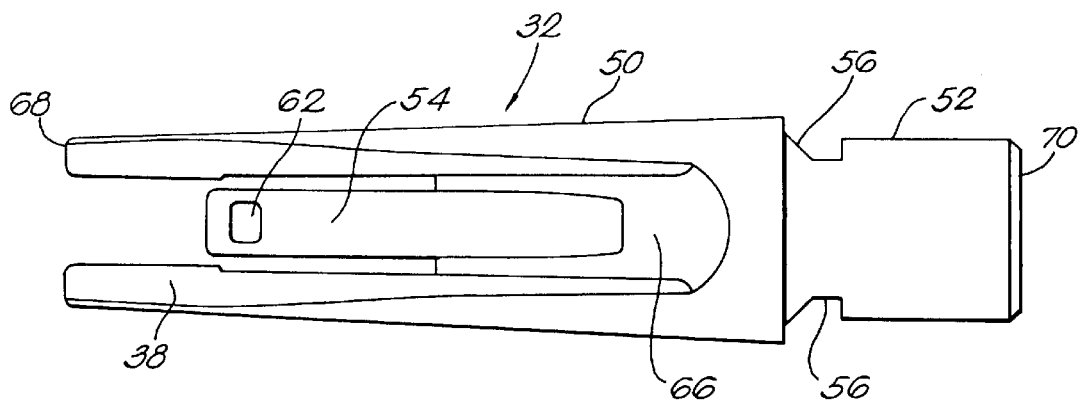
FIG. 3 is a side view perspective of the module housing according to the present invention.
Figure 4:
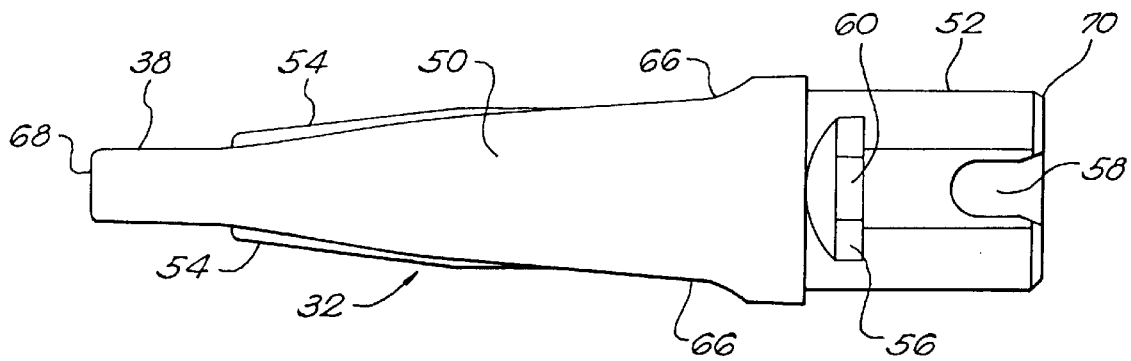
FIG. 4 is a top view perspective of the module housing according to the present invention.
Figure 5:
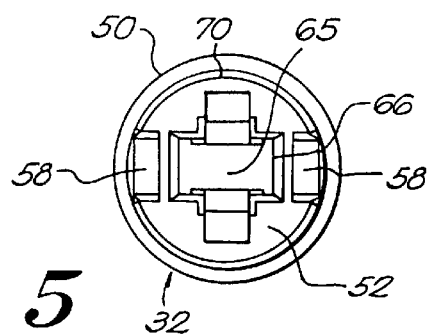
FIG. 5 is a rear view perspective of the module housing according to the present invention.

A more detailed description of the module housing 32 is shown in FIGS. 3–5. Module housing 32 is of a unitary construction in contrast to the two-part construction of the prior art cartridge housing 10. Module housing 32 is preferably made of polycarbonate, however any hard plastic material suitable for housing and applying a ligation clip is felt to fall within the scope of the present invention.

Figure 6:
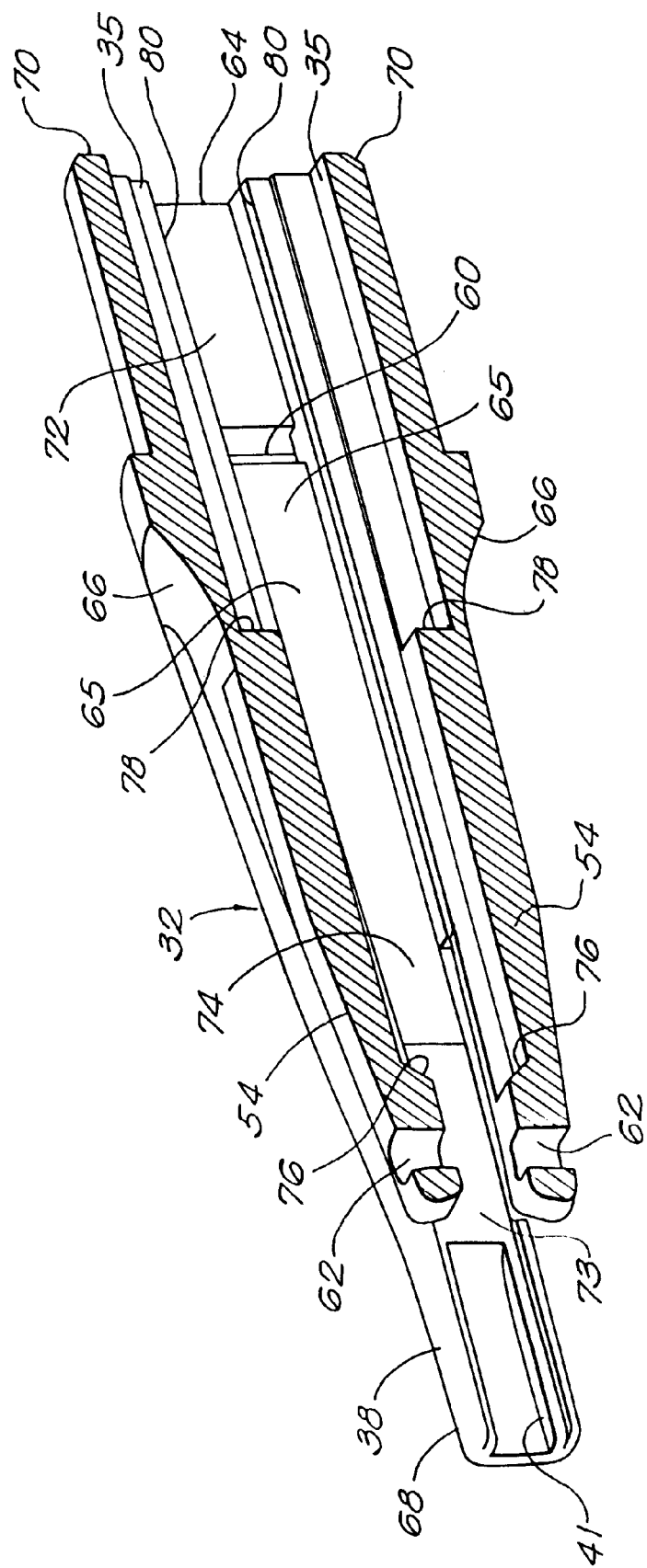
FIG. 6 is a cross section view of the module housing according to the present invention.

As shown in FIG. 3, the frustoconical section 50 of module housing 32 has opposing tapered beveled portions 66 that each form an opposing latch 54 with the distal end of each latch 54 forming a hole 62 thereto. Preferably, the module housing 32 has two opposing latches 54, although in alternative embodiments the housing 32 may have one latch or more than two latches. The distal end of frustoconical section 50 also forms opposing extending arms 38 that are in perpendicular relation to the latches 54. As seen back in FIG. 2, the distal end of extended arms 38 include opposing tips 68 that form flanges that produces a channel 41 (FIG. 6). The channel 41 serves to protect the clip track 28 seated therein during application of the ligation clip 26. The reduced diameter section 52 of module housing 32 has a beveled rear end 70 and two opposing transverse grooves 56 that are diametrically opposed to one another along the distal portion of the reduced diameter section 52. The transverse grooves 56 are used to attach the module 23 to a ligation clip applicator 92, as shall be explained in greater detail below.

As can be seen in FIG. 4, a side view of the module housing 32 shows the opposing latches 54 of the frustoconical section 50 having a higher profile than the opposing beveled portions 66. The frustoconical section 50 has a shape that gradually tapers along substantially its entire length towards its distal end. This gradual tapering of the frustoconical section 50 in combination with beveled portions 66 permits clearer viewing along the longitudinal axis of the module 23 looking towards its distal end since the beveled portions 66 cut away portions of section 50 that would normally obstruct viewing along that particular axis.

The opposing transverse grooves 56 of the reduced diameter section 52 each include a window 60 that extends into the cavity 65 of the module housing 32. Diametrically opposing slot keys 58 are formed on the outer surface of the reduced diameter section 52 and are used to properly orient the module 23 during attachment of the module 23 to the ligation clip applicator 92.

As shown in FIG. 5, the distal end of module housing 32 shows the slot keys 58 in diametrically opposed positions around the reduced diameter section 52. A rear opening 64 is interposed between the two keys 58 and has a cross-like configuration that leads into the cavity 65 inside the module housing 32. The cross-like configuration of rear opening 64 is shaped to receive the pusher 34 during assembly of the module 23, wherein the pusher 34 is inserted into the rear opening 64 until opposing wings 42 of pusher 34 engage respective opposing windows 60 in the module housing 32.

As can be seen in FIG. 6, the cavity 65 forms a first larger channel 72 towards the rear opening 64 of the module housing 32 which is in communication with a second smaller channel 74 at the distal end of housing 32. First larger channel 72 includes a raceway 80 that slidably engages the opposing wings 42 of the pusher 34 and a track 35 that also slidably engages the flanges 46 of the pusher 34. Opposing windows 60 are provided at the sidewalls of the reduced diameter section 52 and form an opening that permits viewing of the cavity 65 from diametrically opposed positions around the reduced diameter section 32. During assembly of the module 23, the pusher 34 is inserted into the rear opening 64 of the module housing 32 until the opposing wings 42 engage respective opposing windows 60. In this orientation, the opposing wings 42 prevent any rearward movement of the pusher 34 so that the pusher 34 cannot be withdrawn form the module housing 32 through the rear opening 64. Further, the junction between the first larger channel 72 and the second smaller channel 74 forms a shoulder 78 that is designed to abut the flanges 46 of the pusher 34 during application of the ligation clip 36 and prevent any further forward movement of the pusher 34 therethrough.

The integral latches 54 form the top and bottom portions of the second smaller channel 74 while the extending arms 38 of the frustoconical section 52 form the side portions of channel 74. As shown back in FIG. 2, slits 55 separate the side and top and bottom portions of the second smaller channel 74 formed between the integral latches 54 and the extended arms 38. The interior portion of the second smaller channel 74 formed by the integral latches 54 also include opposing latch ramps 76 that further restrict the size of channel 74 leading to a front opening 73 of the module housing 32.

Figure 7:
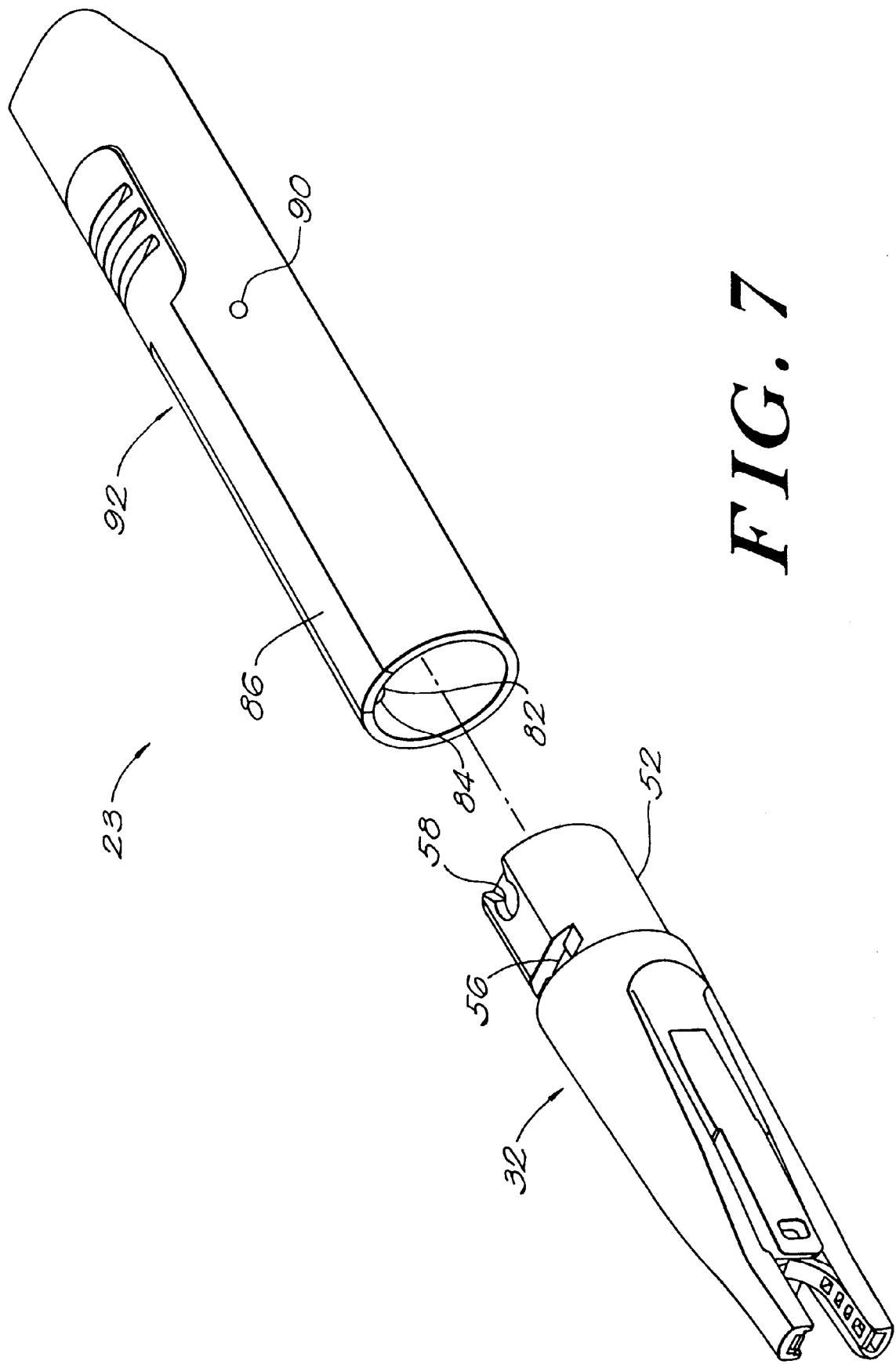
FIG. 7 is a perspective view of the ligation clip module according to the present invention along with a partial perspective of the distal end of a prior art ligation clip applicator.
Figure 8:
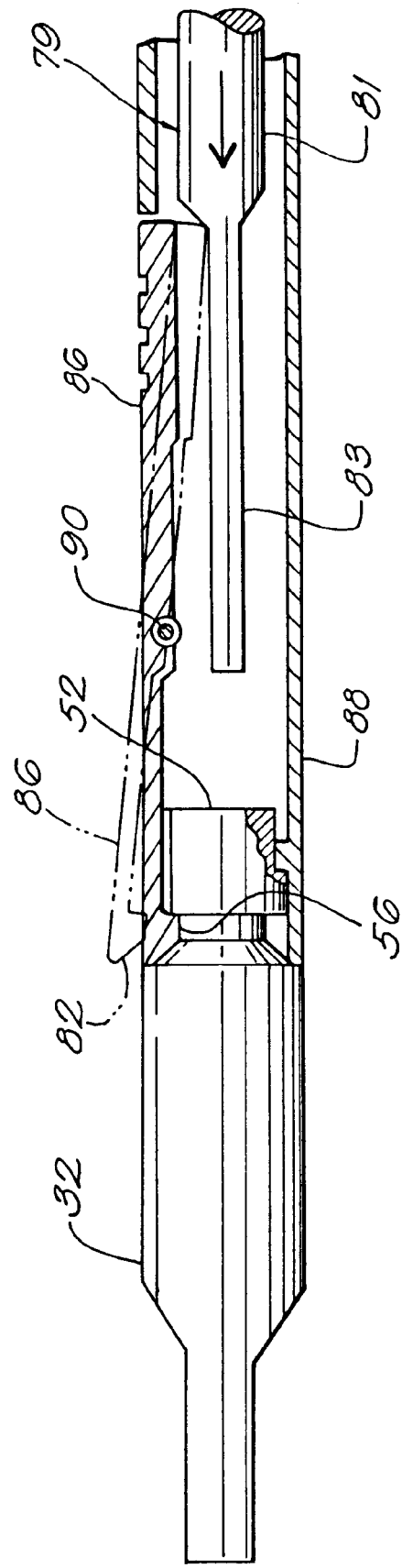
FIG. 8 is a side elevational view, partly in vertical cross-section, of prior art ligation clip applicator illustrating how the ligation clip module according to the present invention is attached to the neck portion of the applicator.

FIG. 7 illustrates the method of attaching the module 23 to the prior art ligation clip applicator 92. The ligation clip applicator 92 connects to module 23 at a hollow shaft 88 of applicator 92. This connection is made at a specific orientation controlled by the arrangement of the slot keys 58 that are arranged at diametrically opposed positions around the reduced diameter section 52. One of the two slot keys 58 must be properly aligned with a key (not shown) formed on the interior surface of the hollow shaft 88 of the ligation clip applicator 92 in order for the module 23 to be attached to the applicator 92. Improper orientation of the slot key 58 will prevent any connection between the module 23 and the ligation clip applicator 92. The hollow shaft 88 also includes a spring-loaded latch 86 that is pivotally mounted on a pivot pin 90 carried on the wall of shaft 88. The distal end of the hollow shaft 88 is provided with a pawl 84. The reduced diameter section 52 fits into the open distal end of the hollow shaft 88. To secure the module 23 in the hollow shaft 88, the proximal end of the spring-loaded latch 86 is pressed down to raise the pawl 84 as shown in phantom in FIG. 8. The module 23 is then inserted and the spring-loaded latch 86 released so that the pawl 84 catches the transverse groove 56 in the reduced diameter section 52 to securely lock the module 23 to the distal end of the hollow shaft 88. Advantageously, the pawl 84 can be provided with a cam surface 82 that rides up on the proximal extreme of the reduced diameter section 52 of the module housing 32. In this way, the cam surface 82 of the pawl 84 is automatically guided to the groove 56 when the module is inserted into the hollow shaft 88. Further discussion related to the attachment of the module 23 is found in U.S. Pat. No. 5,354,304, previously incorporated by reference.

Figure 9:
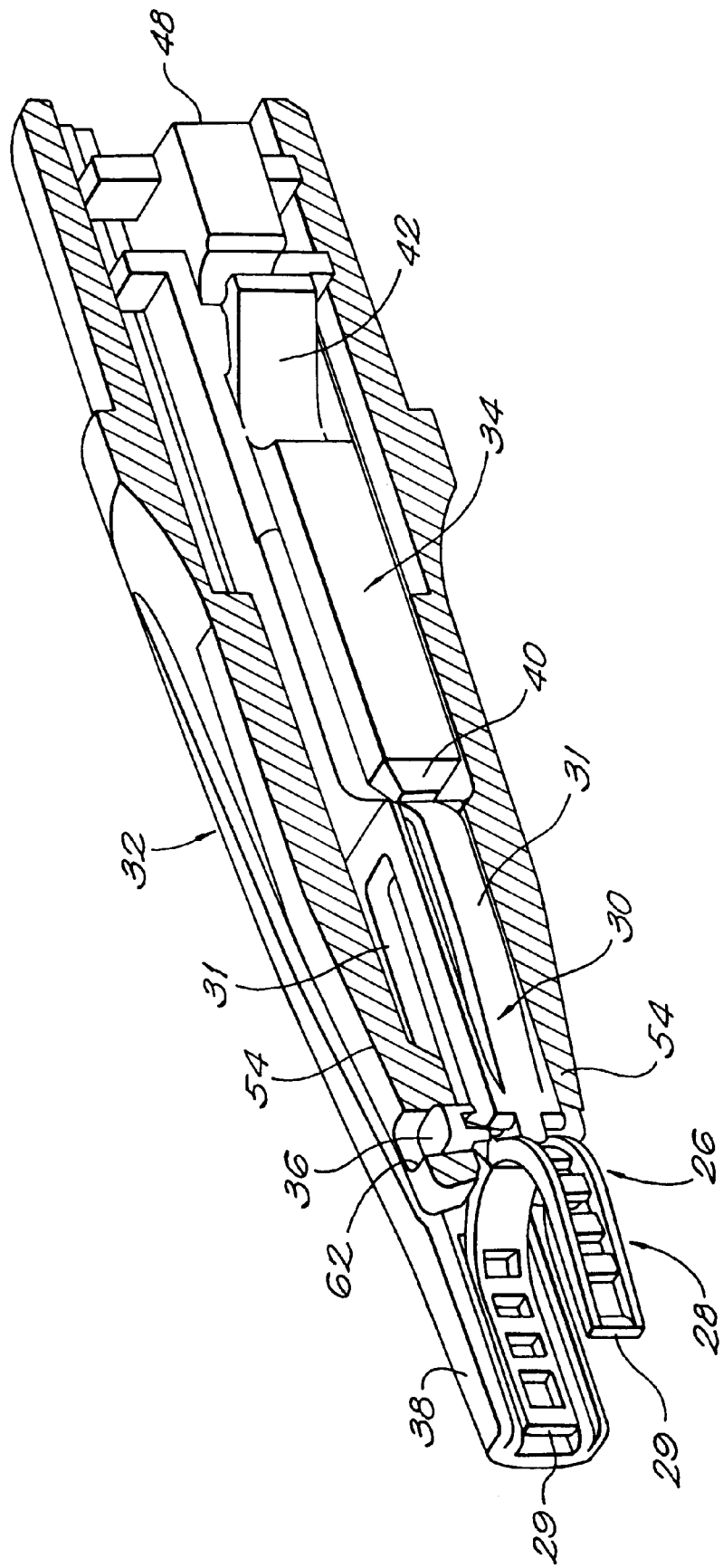
FIG. 9 is a cross section view of the ligation clip module showing a perspective view of the ligation clip and pusher in the initial position after assembly according to the present invention.

FIG. 9 shows the ligation clip 36 loaded in the module housing 32 and ready to be fired by the ligation clip applicator 92. The ligation clip 36 is of the type described in U.S. Pat. No. 4,590,937 and more specifically in U.S. Pat. No. 5,306,283. As explained in detail in '283 patent, the ligation clip 26 is closed by drawing the clip track 28 into the clip body 30 so that the legs 31 of body 30 urge the extensions 29 of the track 28 together. The clip body 30 slides into and is secured within the raceway 80 within the module housing 32. The raceway 80 is defined by straight ribs on both sides of the module housing 32. As described briefly above, post 36 extends from the clip track 28 and is shaped to engage in latch holes 62 formed in the distal ends of the integral latches 54.

In the loaded position shown in FIG. 9, the clip body 30 is positioned within the raceway 80 and the Y-shaped clip track 28 is protected within the opposing arms 38 and the extended tips 68 within the module housing 32, only one of each of which is shown in FIG. 9. The opposing arms 38 of the module housing 32 can be used to manipulate tissue when positioning the ligation clip 26 about a vessel to be ligated. The clip track 28 is also held stationary by the post 36 which are engaged in the latch holes 62 in the latches 54 during manufacturing. In the loaded position, the pusher 34 is positioned behind, and in contact with, the clip body 30 and the opposing wings 42 are engaged with the windows 60 in such a manner that withdrawal of the pusher 34 through the rear opening 64 of the module housing 32 is prevented.

Figure 10:
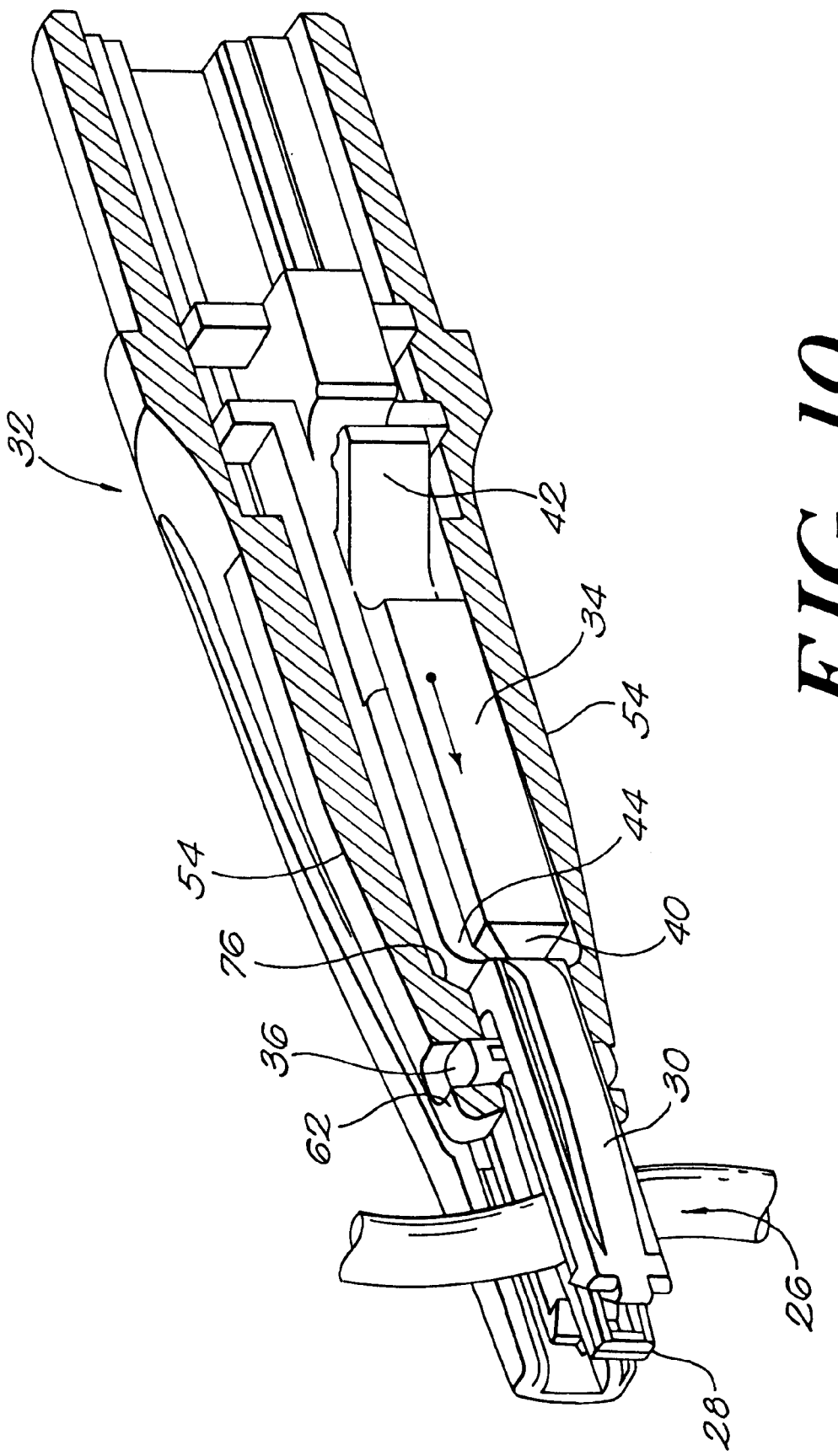
FIG. 10 is a cross section view of the ligation clip module showing a perspective view of the ligation clip and pusher with the latch ramps engaged with the radiused surface of the pusher according to the present invention.

In FIG. 10, the ligation clip 26 is shown in a position around the vessel being ligated after the ligation clip applicator 92 has been actuated. During actuation, the cylindrical portion 83 of the ligation clip applicator 92 engages the rear portion 48 of the pusher 34, thereby forcing the pusher 34 forwardly so that the beveled front end 40 of the pusher 34 contacts the proximal end of the clip body 30 while at the same time engaging the latch ramps 76 of opposing latches 54. The advancement of the pusher 34 also disengages the opposing wings 42 from the windows 60. As the pusher 34 travels forward, the opposing wings 42 ride in the racetrack 80. In this position, the ligation clip 26 is almost fully assembled and the vessel nearly ligated.

Figure 11:
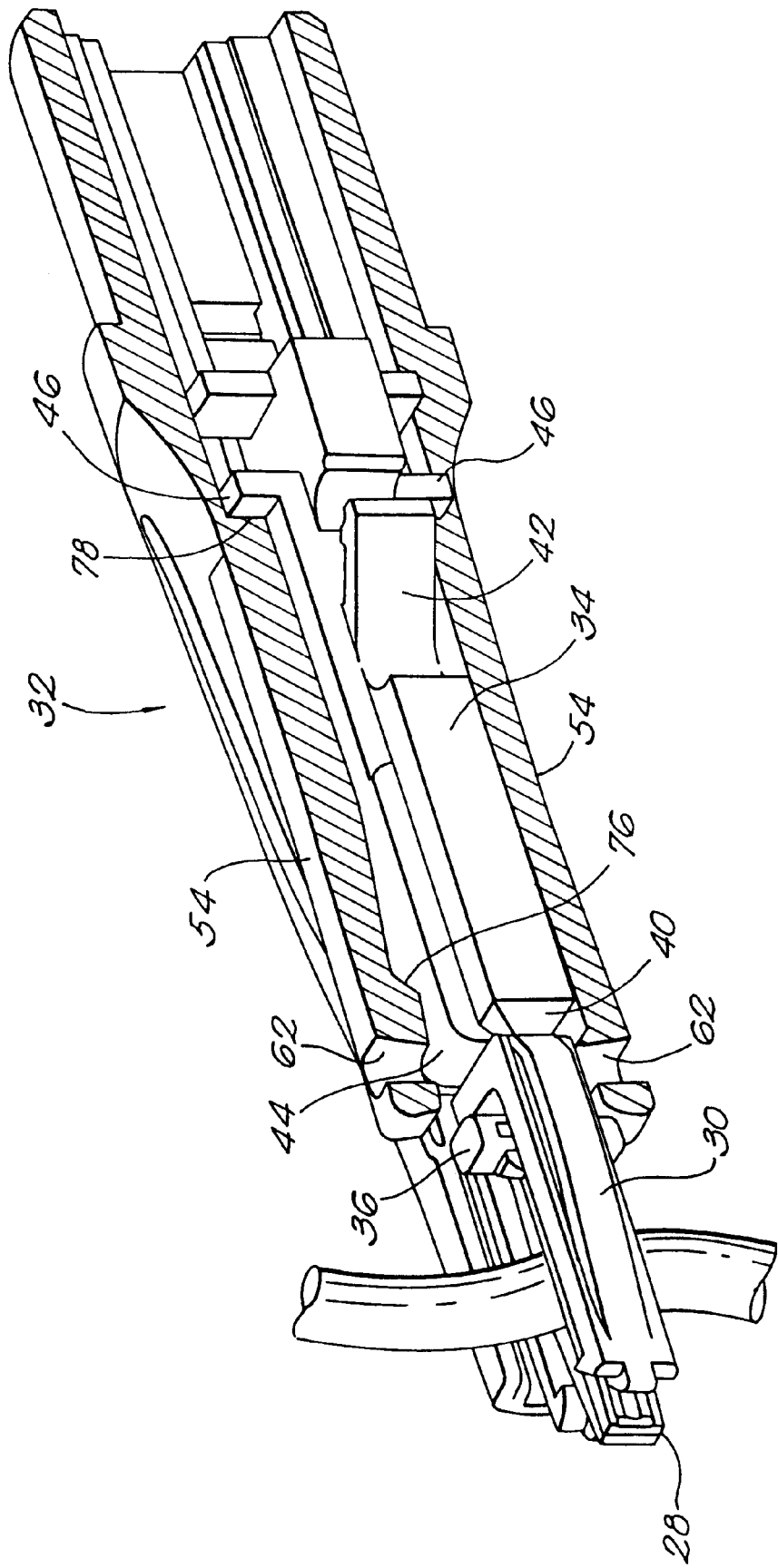
FIG. 11 is a cross section view of the ligation clip module showing a perspective view of the ligation clip and pusher with the ligation clip fully assembled and released according to the present invention.

In FIG. 11, the ligation clip 26 is now fully assembled and the post 36 is disengaged from the latch holes 62 of the opposing latches 54, thereby releasing the clip 26 from the module housing 32. Release is effected by the radiused surfaces 44 of pusher 34 engaging the latch ramps 76 as the pusher 34 is forced forward through the cavity 65 by the cylindrical portion 83. This engagement of the radiused surfaces 44 against the latch ramps 76 pries open the opposing latches 54 and releases the post 36 of the clip body 30 from the latch holes 62. During disengagement of the ligation clip 26, the flanges 46 of the pusher 34 contacts the shoulder 78 of the first larger channel 72, thereby stopping the forward motion of the pusher 34.

After release of the ligation clip 26, the ligation clip applicator 92 may still have sufficient residual actuation remaining in the trigger (not shown) of the applicator 92, especially if the user does not fully pull the trigger during actuation. This condition places the ligation clip applicator 92 in a "fire-thru" mode, whereby the user can further squeeze the trigger of the applicator 92 and apply residual actuation to the module 23. In this mode, the cylindrical portion 83 of the applicator 92 will force the pusher 34 further through the second smaller channel 74, so that the flanges 46 of the pusher 34 are wedged through the smaller opening of the second smaller channel 74 beyond the shoulder 78.

Figure 12:
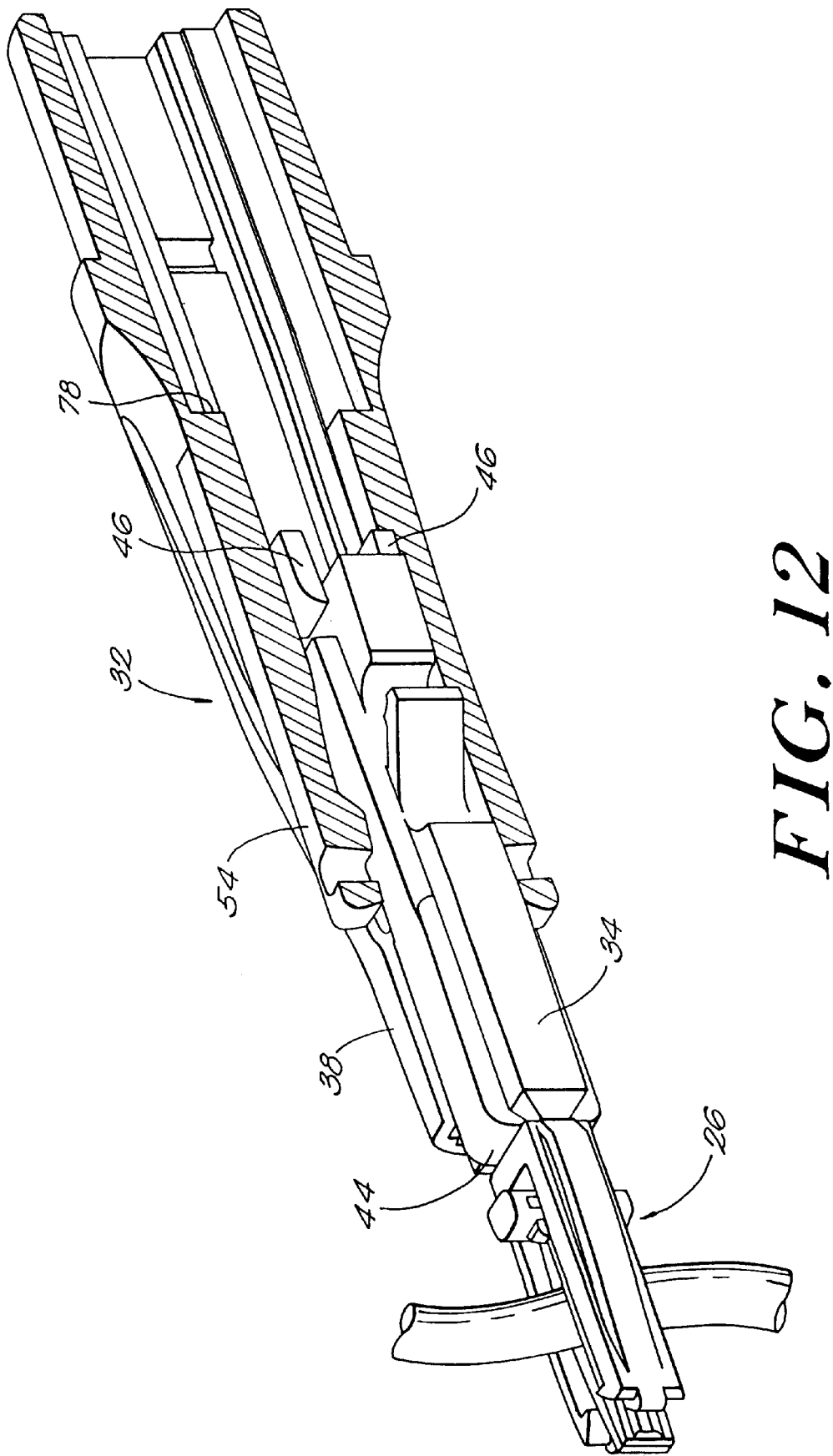
FIG. 12 is a cross section view of the ligation clip module showing the perspective view of the ligation clip and pusher with the module in the "fire-thru" position according to the present invention.

As illustrated in FIG. 12, the "fire-thru" mode of the ligation clip applicator 92 causes the flanges 46 of the pusher 34 to bend inward as the flanges 46 are forced through the smaller opening of the second smaller channel 74. As the pusher is forcibly advanced through the second smaller channel 74, the bent flanges 46 permanently lodge against the side walls of the channel 74 and halt further advancement of the pusher 34. Lodging the pusher 34 within the second smaller channel 74 prevents the pusher 34 from being ejected through the front opening 73 of the module housing 32 and causing possible injury to the patient or the user.

It is within the spirit and scope of the present invention that the module 23 can be constructed to any suitable size or configuration commensurate with the description above to fit different types and sizes of ligation clips. Preferably, the module 23 of the present invention is adapted to house and apply either an 8 mm or 12 mm ligation clips used to ligate a vessel.

Although a specific preferred embodiment of the present invention has been described above in great detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

I claim:

1. A module for mounting a two-part ligation clip having a first part formed to be closed about a vessel and a second part movable relative to the first part to cause the first part to close, said module being operable in conjunction with a ligation clip applicator and comprising:

a module housing;

at least one latch monolithically formed as part of the module housing, said latch holding the first part of the ligation clip in a stationary position relative to the module housing; and a unitary pusher slidingly disposed in said module housing and mounted for advancing movement therein for advancing the second part of the ligation clip relative to the first part to close the first part, said pusher including opposing wings for retaining said pusher in said module housing.

2. The module according to claim 1, wherein said module housing is formed with a tapered beveled along a substantial of its surface, said beveled tapered surface permits clearer viewing along a longitudinal axis of said module housing.

3. The module according to claim 1, wherein said at least one latch includes a latch ramp, said pusher engaging said latch ramp as said pusher is axially slid through said module housing, said latch releasing said first part of the ligation clip when said pusher engages said latch ramp.

4. The module according to claim 1, wherein said module housing is formed with opposing arms for embracing at least a portion of the first part of the ligation clip.

5. The module according to claim 4, wherein said opposing arms terminate in opposing inwardly directed hooks for manipulating tissue to be ligated.

6. The module according to claim 1, wherein said at least one latch is adapted to grip the first part of the ligation clip, the first part of the ligation clip having at least one transversely projecting post and wherein said at least one latch is formed with a hole for receiving the post thereby to provide gripping action.

7. A module for mounting a two-part ligation clip having a first part formed to be closed about a vessel and a second part movable relative to the first part to cause the first part to close, said module being operable in conjunction with a ligation clip applicator and comprising:

a module housing, said module housing forming opposing tapered beveled surfaces, wherein said opposing tapered beveled surfaces permit clearer viewing along a longitudinal axis of said module housing;

at least one latch monolithically formed as part of the module housing for holding the first part of the ligation clip in a stationary position relative to the module; and a pusher operable to axially slidingly move in said module housing, for advancing the second part of the ligation clip relative to the first part to close the first part, wherein the first part of the ligation clip has at least one transversely projecting post and wherein said at least one latch is formed with a hole for receiving the post thereby to provide said holding action.

8. The module according to claim 7, wherein said at least one latch includes a latch ramp, said pusher engaging said latch ramp as said pusher is axially slid through said module housing, said at least one latch releasing said first part of the ligation clip when said pusher engages said latch ramp.

9. The module according to claim 7, wherein said module housing is formed with opposing arms for embracing at least a portion of the first part of the ligation clip.

10. The module according to claim 9, wherein said opposing arms terminate in opposing inwardly directed hooks for manipulating tissue to be ligated.

11. The module according to claim 7, wherein said at least one latch is adapted to grip the first part of the ligation clip, the first part of the ligation clip having at least one transversely projecting post and wherein said at least one latch is formed with a hole for receiving the post thereby to provide gripping action.

12. A ligation clip applicator for applying a two-part ligation clip to a vessel, the ligation clip including a first part formed to be closed about a vessel and a second part movable relative to the first part to cause the first part to close, said applicator comprising:

a module for supporting a two-part ligation clip, said module including a module housing, said module further including at least one latch for holding the first part of the ligation clip in a stationary position relative to said applicator, and a pusher disposed in said module housing and mounted for engaging and advancing the second part of the ligation clip relative to the first part to close the first part;

an activator, mountable with said module, for actuating said pusher, wherein said at least one latch being monolithically formed with said module housing for gripping the first part of the ligation clip; wherein said module housing forms opposing tapered beveled surfaces.

13. The applicator according to claim 12, wherein said module is formed with opposing arms for embracing at least a portion of the first part of said ligation clip.

14. The applicator according to claim 13, wherein said opposing arms terminate in opposing inwardly directing hooks for manipulating tissue to be ligated.

15. The applicator according to claim 12, wherein said opposing tapered beveled surfaces permit clearer viewing along the longitudinal axis of said module housing.

16. The applicator according to claim 12, wherein said at least one latch includes a latch ramp, said pusher engaging said latch ramp as said pusher is axially slid through said module housing during actuation of said pusher, said at least one latch releasing said first part of the ligation clip when said pusher engages said latch ramp.

17. A module for mounting a two-part ligation clip having a first part formed to be closed about a vessel and a second part movable relative to the first part to cause the first part to close, said module being operable in conjunction with a ligation clip applicator and comprising:

a module housing;

at least one latch monolithically formed as part of the module housing, said latch holding the first part of the ligation clip in a stationary position relative to the module housing; and a unitary pusher axially slidingly disposed in said module housing and mounted for advancing movement therein for advancing the second part of the ligation clip relative to the first part to close the first part.

18. The module according to claim 17, wherein said module housing is formed with a tapered beveled surface, said beveled tapered surface permits clearer viewing along a longitudinal axis of said module housing.

19. The module according to claim 17, wherein said at least one latch includes a latch ramp, said pusher engaging said latch ramp as said pusher is axially slid through said module housing, said latch releasing said first part of the ligation clip when said pusher engages said latch ramp.

20. The module according to claim 17, wherein said module housing is formed with opposing arms for embracing at least a portion of the first part of the ligation clip.

21. The module according to claim 20, wherein said opposing arms terminate in opposing inwardly directed hooks for manipulating tissue to be ligated.

22. The module according to claim 17, wherein said at least one latch is adapted to grip the first part of the ligation clip, the first part of the ligation clip having at least one transversely projecting post and wherein said at least one latch is formed with a hole for receiving the post thereby to provide gripping action.

* * * * *